United States Patent
Dadlani Mahtani et al.

(10) Patent No.: US 11,081,213 B2
(45) Date of Patent: Aug. 3, 2021

(54) PERSONALIZING PATIENT PATHWAYS BASED ON INDIVIDUAL PREFERENCES, LIFESTYLE REGIME, AND PREFERENCES ON OUTCOME PARAMETERS TO ASSIST DECISION MAKING

(71) Applicant: KONINKLIJKE PHILIPS N.V., Eindhoven (NL)

(72) Inventors: Pavankumar Murli Dadlani Mahtani, Eindhoven (NL); Jingyu Zhang, Elmsford, NY (US); Sebastian Peter Michael Dries, Hamburg (DE); Colleen Michelle Ennett, White Plains, NY (US); Joerg Sabczynski, Norderstedt (DE); Beant Kaur Dhillon, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 464 days.

(21) Appl. No.: 14/427,660

(22) PCT Filed: Sep. 25, 2013

(86) PCT No.: PCT/IB2013/058834
§ 371 (c)(1),
(2) Date: Mar. 12, 2015

(87) PCT Pub. No.: WO2014/049527
PCT Pub. Date: Apr. 3, 2014

(65) Prior Publication Data
US 2015/0254408 A1    Sep. 10, 2015

Related U.S. Application Data

(60) Provisional application No. 61/706,999, filed on Sep. 28, 2012.

(51) Int. Cl.
*G16H 10/60* (2018.01)
*G16H 20/00* (2018.01)
(Continued)

(52) U.S. Cl.
CPC ............ *G16H 10/60* (2018.01); *G16H 20/00* (2018.01); *G16H 70/40* (2018.01); *G16H 50/20* (2018.01); *G16H 80/00* (2018.01)

(58) Field of Classification Search
CPC ..... G06F 19/322; G06F 19/345; G06Q 50/24; G06Q 50/22; G06Q 10/10; G06Q 10/00; G06Q 10/06; G06Q 30/00
(Continued)

(56) References Cited

U.S. PATENT DOCUMENTS 5,953,704 A    9/1999  McIlroy et al.
6,434,531 B1 *  8/2002  Lancelot ............... G06F 19/325
                                                              705/3

(Continued)

FOREIGN PATENT DOCUMENTS

WO    2011088191 A2    7/2011

OTHER PUBLICATIONS

Raats, C.J.I. et al. "A generic tool for development of decision aids based on clinical practice guidelines" Patient Education and Counseling, Elsevier, Amsterdam, N> vol. 73, No. 3, Dec. 2008, pp. 413-417.*

(Continued)

*Primary Examiner* — Rachel L. Porter

(57) ABSTRACT

A system (10) for personalization of patient pathways and treatment options includes a patient information database (32) which stores patient data relating to a patient's medical records. A patient personalization system (12) receives the patient's lifestyle values and preferences and evaluates choices of pathways and treatments and a clinical decision (Continued)

support system (18) generates choices of pathways and treatments from the patient data and the patient's lifestyle values and preferences.

3 Claims, 4 Drawing Sheets

(51) Int. Cl.
*G16H 70/40* (2018.01)
*G16H 50/20* (2018.01)
*G16H 80/00* (2018.01)

(58) Field of Classification Search
USPC .......................................... 705/2–3
See application file for complete search history.

(56) References Cited

U.S. PATENT DOCUMENTS

| 8,655,682 | B2* | 2/2014 | Srivastava | G16H 70/20 |
| | | | | 705/3 |
| 10,593,000 | B2* | 3/2020 | Op Den Buijs | G16H 20/00 |
| 2002/0184050 | A1 | 12/2002 | Papageorge | |
| 2005/0273364 | A1 | 12/2005 | Raab | |
| 2006/0218007 | A1* | 9/2006 | Bjorner | G06Q 10/10 |
| | | | | 705/2 |
| 2007/0198296 | A1 | 8/2007 | Pellinat et al. | |
| 2008/0172214 | A1* | 7/2008 | Col | G06Q 50/24 |
| | | | | 703/11 |
| 2011/0093288 | A1* | 4/2011 | Soto | G16H 15/00 |
| | | | | 705/2 |
| 2011/0301977 | A1 | 12/2011 | Belcher | |
| 2012/0047105 | A1* | 2/2012 | Saigal | G06N 5/048 |
| | | | | 706/52 |

OTHER PUBLICATIONS

Langlotz, C.P. et al. "Adapting a consultation system to critique user plans". Int. J. Man-Machine Studies (1983) 19, 479-496.
Weinstein, M.C. et al. "QALYs: The Basics". Value in Health, vol. 12, Suppl. 1, 2009.

* cited by examiner

PERSONALIZING PATIENT PATHWAYS BASED ON INDIVIDUAL PREFERENCES, LIFESTYLE REGIME, AND PREFERENCES ON OUTCOME PARAMETERS TO ASSIST DECISION MAKING

CROSS-REFERENCE TO PRIOR APPLICATIONS

This application is the U.S. National Phase application under 35 U.S.C. § 371 of International Application No. PCT/IB2013/058834, filed on Sep. 25, 2013, which claims the benefit of U.S. Provisional Application No. 61/706,999, filed on Sep. 28, 2012. These applications are hereby incorporated by reference herein.

The present application relates to clinician and patient decision making. It finds particular application in conjunction with systems and methods for providing personalized patient treatment decision support and patient pathways and will be described with particular reference thereto. However, it is to be understood that it also finds application in other usage scenarios and is not necessarily limited to the aforementioned application.

Shared decision making is an approach where clinicians and patients make informed decisions together using the best available evidence when facing the task of making medical decisions. Shared decision making increases the patient's participation to take informed health care choices by providing them with tailored information on alternative options for diagnosis and treatment. Typically, shared decision making is performed with the help of patient decision support tools or patient decision aids. With the help of these patient decision support tools, patients get a better understanding about the disease status, patient education is more unbiased and consistent in quality, and decisions are made with better quality. Existing patient decision support tools focus on providing educational information from trusted sources to the patients, asking patients to specify their own preferences and values, and having the patients discuss with clinicians the information they obtained to reach a decision that is understood and agreed to by the patients. However, existing patient decision support tools are not personalized, so they can only provide information based on the general population.

For example, when a patient is diagnosed with a particular type of cancer, a team of multidisciplinary clinicians sit together and discuss the case to determine which treatment options are available. Soon after, a clinician sits together with the patient and discusses the diagnosis and available treatment options. The clinician and patient then jointly decide on a recommended treatment and patient pathway which is based on clinical guidelines. However, this choice of treatment and pathway is generic and based on known medical practices and does not take into account information beyond pathology, symptoms, and other clinical parameters. Thus, there are no truly personalized pathways that use the patient's preferences and lifestyle habits.

Furthermore, it is a well-known problem that patients do not fully understand what options are available to them and what the consequences of those options mean for them in particular. While current decision aids (e.g. paper-based value clarification forms, web-based tools, etc.) take into account to some extent the health outcome (including recovery and side effects) and the patient's values towards the side effects, they do not fully consider the lifestyle regime of the patient. Furthermore, these tools are manually based and disentangled to other sources of information. Additionally, many shared decisions are based on verbal discussions, which are difficult for patients to fully grasp all the information or even fully understand.

In addition, there is no interactive solution that allows patients to further personalize their treatment and clinical pathway based on personal preferences of outcome parameters (e.g. side effects, time of recovery, etc.), such that they can visually see changes of their patient pathway based on changing outcome parameters, or adjust their patient pathway (e.g. make treatment less frequent) and view the effect of those changes on the outcome parameters.

Additionally, patients and clinicians are often faced with making difficult treatment decisions based on information collected as part of standard diagnostic procedures. As additional or new diagnostic tests become available, it is challenging to integrate this information into existing decision aids, which may help the patient and/or the clinician to determine the optimal treatment plan for the current patient.

The present application provides new and improved methods and systems which overcome the above-referenced problems and others.

In accordance with one aspect, a system for personalization of patient pathways and treatment options is provided. The system includes a patient information database which stores patient data relating to a patient's medical records, a patient personalization system which receives the patient's lifestyle values, and a decision support system which evaluates the choices of pathways and treatments from the patient data and the patient's lifestyle values and preferences.

In accordance with another aspect, a system for personalizing patient pathways and treatment options is provided. The system includes one or more processors programmed to receive patient data relating to a patient's medical records, receive the patient's lifestyle values and preferences from the patient, generate a choice of patient pathway and treatment options from the patient data and the patient's lifestyle values and preferences, and generate a graphical tool to evaluate and compare the choice of pathway and treatment options.

In accordance with another aspect, a method for personalization of patient pathways and treatment options is provided. The method includes receiving patient data representing a patient's medical record, estimating probabilities of mortality and morbidity from the patient data, calculating probabilities of having long term impairments or disabilities based on the probabilities of morbidity, surveying the patient using time-trade-off to weigh the possible long-term impairments or disabilities, calculating an expected quality-adjusted life years (QALYs) and confidence interval of alternative choices using the trade-off weighing the possible long-term impairments or disabilities, and displaying the alternative choices, QALYs, and confidence intervals in a graphical tool.

One advantage resides in providing personalized treatment and patient pathways.

Another advantage resides in providing alternative options for diagnosis and treatment.

Another advantage resides in quantitatively evaluating and comparing alternative choices to assist in making personalized decisions.

Another advantage resides in improving patient care.

Still further advantages of the present invention will be appreciated to those of ordinary skill in the art upon reading and understanding the following detailed description.

The invention may take form in various components and arrangements of components, and in various steps and arrangements of steps. The drawings are only for purposes of illustrating the preferred embodiments and are not to be construed as limiting the invention.

FIG. 1 is a block diagram of an information technology (IT) infrastructure in accordance with the present application.

The present application is directed to a decision support system which quantitatively evaluates and compares alternative choices of diagnosis and treatment from a patient's perspective to find the best personalized medical decision. In one embodiment, the decision support system utilizes an algorithm to convert prognosis and clinical outcomes, such as probability of mortality and morbidities, into values that are directly meaningful for the patient in evaluating and comparing different choices from the patient's perspective. The input parameters of the system include patients' personal medical records, clinical evidences on outcomes and prognosis for the appropriate population, patients' values and preferences, and the like. The output of the system is a quantitative evaluation and comparison of the alternative choices and a simple straightforward treatment recommendation. If the patient requests, the system can provide additional outputs including traditional educational materials, information and access to a large patient community, probabilities of all the alternative options to be the best, confidence intervals of all the estimations, and the evidences the computation is based on.

The decision support system also enables patients to compare alternative choices on the same measure, such as allowing the patients to adjust for lifestyle regime and preferences, outcome parameters, patient pathways, QALYs, desired probability of an overall outcome or of a specific outcome parameter, and the like. The system can also provide details about the sources of the parameters and the model and mathematics underlying the computation if patients are interested. The present application simplifies the shared decision making process for the patient and clinician, reduces patient's stress, increases the patient's satisfaction of their decisions, ensures and improves decision quality, reduces clinician's workload, increases quality and efficiency of the education provided to patients, increases clinician's confidence, and reduces overall healthcare costs.

The decision support system also quantifies whether potential new information derived from an additional or new diagnostic test will help to determine the optimal treatment plan. By incorporating provider-specific treatment delivery statistics, the decision support system provides estimates of how successful the treatment plan will be for this patient with a specific care provider. The decision support system also allows care providers to establish confidence interval limits prior to showing the results to the patient. Another option is for the care provider to assess the sources of the information used to determine the optimal treatment option to ensure that the sources are relevant to the current patient.

Figure 1:
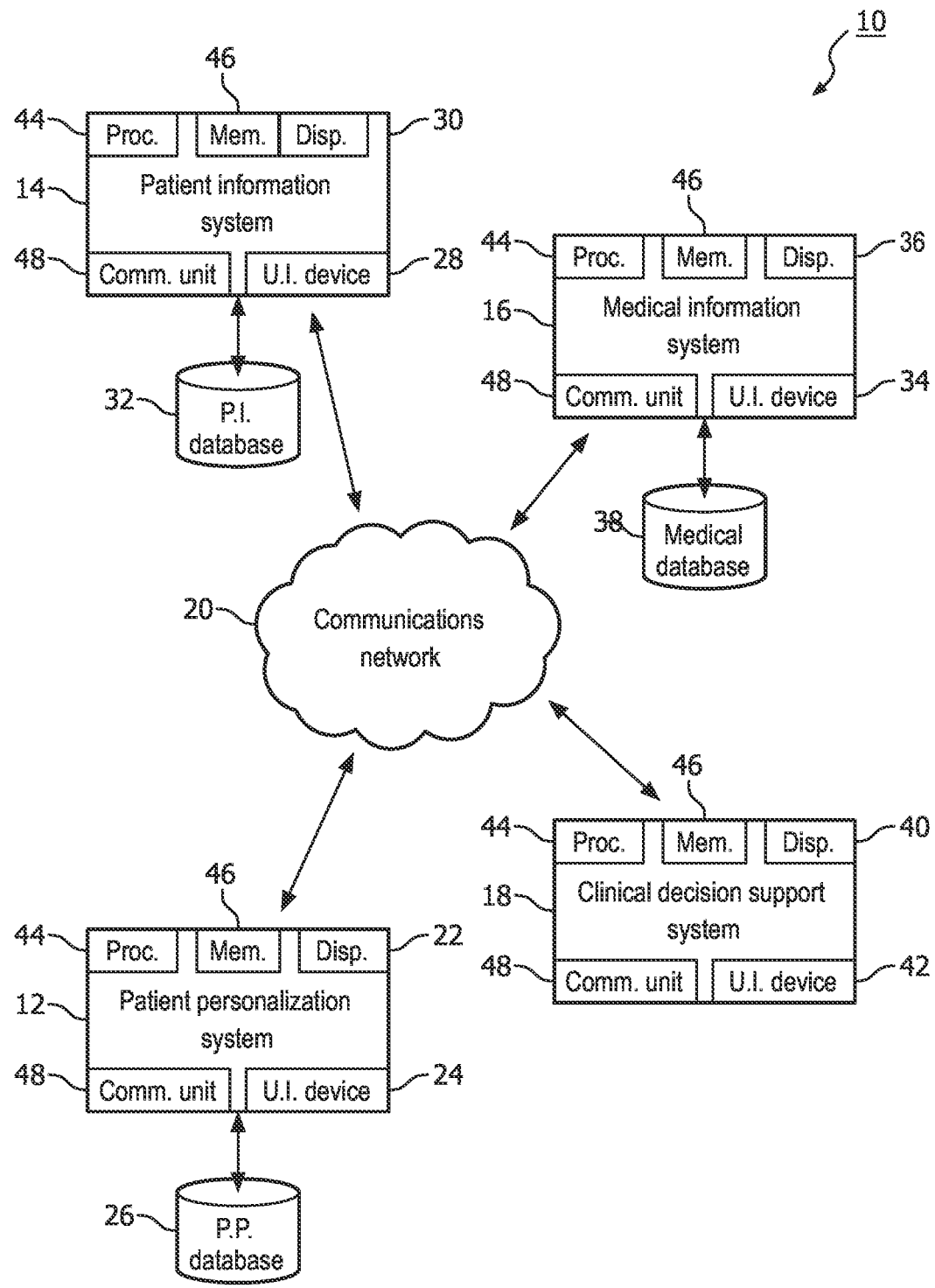

With reference to FIG. 1, a block diagram illustrates one embodiment of an IT infrastructure 10 of a medical institution, such as a hospital. The IT infrastructure 10 suitably includes a patient personalization system 12, a patient information system 14, one or more medical information systems 16, a decision support system (DSS) 18, and the like, interconnected via a communications network 20. It is contemplated that the communications network 20 includes one or more of the Internet, Intranet, a local area network, a wide area network, a wireless network, a wired network, a cellular network, a data bus, and the like. It should also be appreciated that the components of the IT infrastructure be located at a central location or at multiple remote locations.

The patient personalization system 12 enables the patient to input the patient values, lifestyle regimes, and preferences related to diagnosis and treatment from a patient's perspective. The patient personalization system 12 also receives a quantitative evaluation and comparison of the alternative choices of treatment and pathways to the patient (not shown) being treated in the medical institution. For example, the patient personalization system 12 displays the quantitative evaluation and comparison of the choices of treatment and pathways including a comparison of alternative choices on the same measure, such as allowing the patients to adjust for lifestyle regime and preferences, outcome parameters, patient pathways, QALYs, desired probability of an overall outcome or of a specific outcome parameter, and the like. The patient personalization system 12 includes a display 22 such as a CRT display, a liquid crystal display, a light emitting diode display, to display the evaluation and/or comparison of choices and a user input device 24 such as a keyboard and a mouse, for the patient to input the patient values and preferences and/or modify the evaluation and/or comparison. In one embodiment, the patient values and preferences are stored in the patient personalization database 26. Examples of patient personalization systems 12 include, but are not limited to, a software application that could be accessed and/or displayed on a personal computer, web-based applications, tablets, mobile devices, cellular phones, and the like.

The patient information system 14 stores patient data related to the patient being treated by the medical institution. The patient data include the patient's medical records, patient demographics such as weight, age, family history, co-morbidities, and so on. The patient data may also include physiological data collected from one or more sensors, physiological data, laboratory data, imaging data acquired by one or more imaging devices, the patient's administrative data, the patient's medical records, and the like. In one embodiment, the patient data include the patient's values, lifestyles regimes, and preferences stored in the patient personalization database 26. Further, the patient data can be generated automatically and/or manually. As to the latter, user input devices 28 can be employed. In some embodiments, the patient information systems 14 include display devices 30 providing users a user interface within which to manually enter the patient data and/or for displaying generated patient data. In one embodiment, the patient data are stored in the patient information database 32. Examples of patient information systems include, but are not limited to, electronic medical record systems, departmental systems, and the like.

Similarly, the medical information system 16 stores medical data collected from a population that is related to the patient being treated. For example, the medical information system 16 stores population level medical data relating to various clinical problems of differing populations. The medical data include population level knowledge from literature, retrospective studies, clinical trials, clinical evidence on outcomes and prognosis, and the like. Further, the medical data can be generated automatically and/or manually. As to the latter, user input devices 34 can be employed. In some embodiments, the medical information systems 16 include display devices 36 providing users a user interface within which to manually enter the medical data and/or for displaying generated medical data. In one embodiment, the medical data are stored in the medical database 38. In another embodiment, the patient data are also stored in the medical database 38. Examples of medical information systems include, but are not limited to, medical literature databases, medical trial and research databases, regional and national medical systems, and the like.

In another embodiment, the DSS 18 stores clinical models and algorithms embodying the clinical support tools or patient decisions aids. The clinical models and algorithms typically include one or more diagnosis and/or treatment options as a function of the patient data and the clinical problem of the patient being treated. Further, the clinical models and algorithms typically include recommendations for the various diagnosis and/or treatment options based on the state of the patient and the patient data. Specifically, the clinical models and/or guidelines are determined diagnoses and/or treatment options for patients with specific diseases or conditions based on the best available evidence, i.e., based on clinical evidence acquired through scientific method and studies, such as randomized clinical trials. After receiving patient data, the DSS 18 applies the clinical model and algorithm pertinent to the clinical problem of the patient being treated. The DSS 18 then provides the available diagnoses and/or treatment options based on the patient data. It should also be contemplated that as more patient data becomes available, the DSS 18 updates the diagnosis and/or treatment options available to the patient. Specifically, the DSS 18 acquires patient data, medical data, clinical models and algorithms, and the like and provides a quantitative evaluation and comparison of the alternative choices of treatment and pathways to the patient (not shown) being treated in the medical institution. For example, the DSS 18 acquires the patient's medical records from the patient information system 14, clinical evidences on outcomes and prognosis for the appropriate population from the medical information system 16, the clinical models and algorithms, patient values, lifestyle regimes, and preferences input by the patient, and displays the quantitative evaluation and comparison of the choices of treatment and pathways. The DSS 18 includes a display 40 such as a CRT display, a liquid crystal display, a light emitting diode display, to display the clinical models and algorithms and a user input device 42 such as a keyboard and a mouse, for the clinician to input and/or modify the clinical models and algorithms.

The components of the IT infrastructure 10 suitably include processors 44 executing computer executable instructions embodying the foregoing functionality, where the computer executable instructions are stored on memories 46 associated with the processors 44. It is, however, contemplated that at least some of the foregoing functionality can be implemented in hardware without the use of processors. For example, analog circuitry can be employed. Further, the components of the IT infrastructure 10 include communication units 48 providing the processors 44 an interface from which to communicate over the communications network 20. Even more, although the foregoing components of the IT infrastructure 10 were discretely described, it is to be appreciated that the components can be combined.

As mentioned above, the DSS 18 receives recommended patient pathway(s) or treatment option(s) utilizing the available patient data, medical data, clinical models and algorithms, patient's preferences on outcome parameters (e.g. on severity of side effects, frequency of treatment, survival prediction after treatment, risk estimation for complication after treatment, etc.) and the patient's lifestyle regime (agenda, habits, diet, exercise, risk estimations for long-term impairment and disabilities after treatment, etc.). Thus, the DSS 18 takes into account not only the values that the patient has on outcome parameters but further personalizes it to the patient's needs and context.

In one embodiment, the DSS 18 generates a graphical tool that allows patients to visualize the tailored patient pathway(s) or treatment option(s) that were generated based on the input as described above. The graphical tool portrays visually the personalized patient pathway(s) and visual trends on the health outcome for each (or the selected) pathway or treatment option, including the time of recovery, the consequences (e.g. physical, mental, emotional), the frequency and regime of the treatment, the main lifestyle changes and other adverse effects (e.g. dietary, sleep, tiredness, sex life, etc.). In a further embodiment, the patient is able to have control and further personalize the graphical tool by graphically adjusting any one of the above parameters to visualize the effect of that change on the trends of the other outcome parameters and on the patient pathway. Alternatively, the user can graphically adjust the pathway and view the effects of that change on the trends of all outcome parameters.

The graphical tool also portrays the probability of overall outcome based on available medical evidence from the medical data and the clinical models and algorithms. In one embodiment, the patient is able to adjust the probability of outcome and see the effect of change on all parameters and patient pathways. In addition to the probability of overall outcome, other probabilities (based on available evidence) of specific outcome parameters can be added: e.g. likelihood of the specific trend of decline in physical energy, likelihood of the recovery, likelihood of physical pain, etc. Additional information can also be shown of how frequent or practiced the particular patient pathway is, which can also be adjusted by the patient to view for example the most frequent pathway used. In the case where the available evidence is not available for that particular probability value(s), the system automatically searches for the nearest available evidence and indicates it to the user.

In another embodiment, the graphical tool allows patients to visually explore the outcome parameters of a particular patient pathway or treatment option over time, i.e., recovery of the cancer and side effects. Patients can either click at any particular point on the visual patient pathway or adjust a specific visual control tool (e.g. a visual slider over time) to visualize e.g. the size/spread of the cancer; visualize the side effects such as amount of hair loss, etc. Furthermore, the visuals can be coupled with a probability of such outcome, such that the user is able to adjust the probability value and view the changed visuals.

Specifically, in one embodiment, the DSS 18 translates prognosis and clinical outcomes such as probabilities of mortality and different morbidities into quantitative decision evaluation and comparison from the patient perspective. The evaluation relies on the available patient data, medical data, clinical models and algorithms, patient's preferences on outcome parameters, the patient's lifestyle regime, and the like. In another embodiment, the DSS 18 enables patients to evaluate and compare alternative decision choices using the same measure combining length of survival and quality of life according to their own preference. This leads to a direct, simple, personal, and quantitative decision support tool for the patients. In another embodiment, the DSS 18 also provides details about the sources of the parameters, the way of calculation if patients are interested, and any other related educational materials. For example, the DSS 18 provides more quantitative evaluations and comparisons of different alternative choices and decision support that can directly help the patient to easily answer the difficult questions they face. The choices are evaluated in terms of QALYs which consider both length of survival and quality of life from the patient perspective and the confidence intervals.

To accomplish this, the DSS 18 utilizes the patient data, clinical models and algorithms, medical data, and the like to compute optimal patient pathways and/or treatment options for the patient given their current condition. Specifically, the clinical model and algorithm are applied to the patient to determine the available patient pathways and/or treatments. The patient's preferences, lifestyle regimes, and values are then utilized in estimating the parameters for computing a comparable measure that trades off survival and quality of life for each of the pathways and/or treatment options based on the medical data of related populations.

Figure 2:
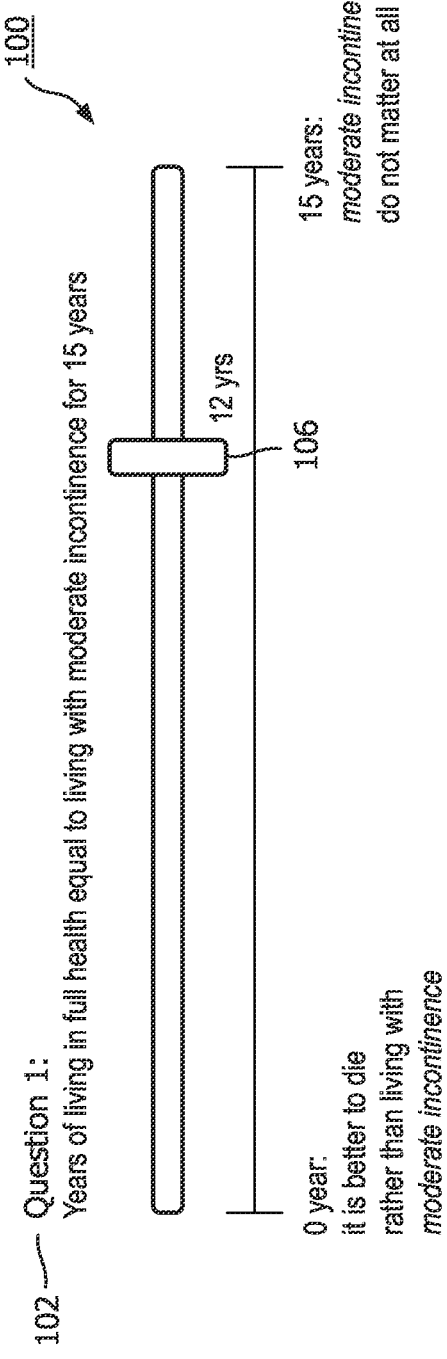
FIG. 2 is an interface for quantitatively determining the tradeoff of quality of life and length of survival in accordance with the present application.
Figure 2:
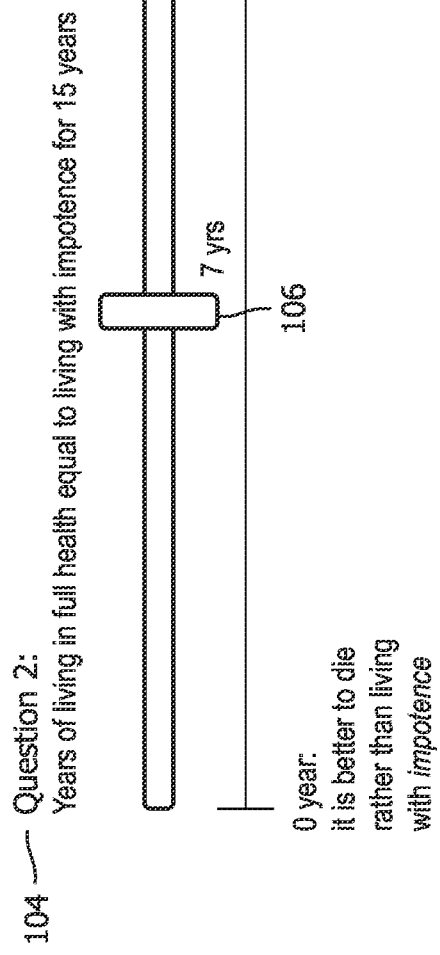

The key role of personal preference and value assessment is to understand the patient's preference and make the best use of these preferences in the decision making process. For example, a survey or questionnaire determines the preference by trading off time of living in perfect health and living with different impairments. The time-trade-off survey results in a personalized and comparable measure, quality of life, for different impairments or disabilities. Furthermore, the integral of quality of life over time results in a comparable measure, QALY, which enables patients and physicians to directly compare different choices according to the patient's own preference. As shown in FIG. 2, the personalization system 12 includes an interface 100 for quantitatively determining the tradeoff of quality of life and length of survival is illustrated. For example, imagine that the patient has low-grade localized prostate cancer at the age of 70. If treated by radical prostatectomy, the patient has 15 years to live but with moderate incontinence and impotence (common long-term impairments due to radical prostatectomy). The interface 100 includes a questionnaire which enables the patient to indicate how long they would like to live with moderate incontinence 102 and impotence 104. The patient can choose to live these 15 years with moderate incontinence and impotence or the patient can choose to give up some of their life years to live for a shorter period in full health. The cross 106 on the line indicates the number of years in full health that the patient thinks is of equal value to 15 years with moderate incontinence and impotence.

During or after treatment, patients can enter subjective data (e.g. fill in questionnaires) or patient reported outcomes, and clinicians can enter progress information with regard to the ailment (e.g. tumor reduction size), to compare how effective the treatment is (chosen patient pathway) compared to the expected recovery and side effects based on available evidence, to further understand and even graphically visualize the effectiveness and progress of the treatment. This can be done at any particular point in the patient pathway, once treatment has been initiated. For example, imaging results or patient data at different points or stages of treatment can be uploaded to the system and used to make a comparison with the expected outcome (images or pictures stored in the knowledge base of medical evidence) and produce a treatment effectiveness or progress score. Using patient reported outcome data, the system can visually portray differences between the actual trends of recovery and side effects, and the expected trends based on available evidence.

For all the different options, the DSS 18 also estimates clinical outcomes such as probability of death and probabilities of morbidities based on the patient's disease status utilizing the clinical models and algorithms and medical data. To accomplish this, the DSS 18 assesses the QALY outcomes of different morbidities according to patient's preference and value. The QALY outcomes of different decision choices of the patients are then evaluated. These QALY outcomes are quantitative, comparable, and personalized and presented to the patient. In order to not overwhelm patients, the results and the evidences can be provided at different levels. For example, in one embodiment, the most direct result (i.e., the expected QALYs of the different treatments) is displayed with other details available if the patients are interested. In another embodiment, the expected QALYs and corresponding confidence intervals are computed under different alternative actions for the patients given their current condition according the medical data and clinical models and algorithms. In another embodiment, the confidence interval of the expected QALYs is computer via stochastic sensitivity analysis. It should be appreciated that unlike the probability of mortality, which is traditionally a focus of clinical research and can be usually found from literature for different population, probabilities of impairments/disabilities are computed from the probabilities of complications or side effects of each specific alternative action to choose. Risks of mortality and morbidities can be obtained by either counting patients in the longitudinal dataset from the clinical provider or directly using values provided in the medical literature for the population to which the patient belongs.

In another embodiment, the DSS 18 provides additional diagnostic tests and/or provider-specific treatment delivery statistics into the patient personalized decision making process. Currently, decision support tools use a set of standard diagnostic tests (digital rectal exam (DRE), Gleason Score, Prostate-Specific Antigen (PSA) test and tumor grade) that reflect the most impactful independent parameters that the available evidence on treatment outcomes was generated upon. With "advanced" or otherwise additional diagnostic tests being available to further specify a patient's precondition, and/or with provider-specific treatment delivery statistics instead of general outcomes from literature, the discrimination between the therapeutic alternatives might be improved (e.g., in terms of narrower confidence intervals for the outcome predictions) that would then make some or all alternatives distinctively ranked. For example, the "advanced" diagnostic tests may include Dx (m-p) MRI, image-fusion, ultrasound elastography, HistoScan, PCA3, and the like. If confidence intervals cannot be narrowed enough to provide additional discriminatory power of treatment options, the DSS 18 can inform the patient that these additional advanced tests are unnecessary for the specific patient.

In a further embodiment, the DSS 18 enables the care provider to adjust the confidence interval limits to adjust for difficult to capture information about the patient that would change the ranking of the treatment options. For example, if the patient had prior radiation therapy for a different tumor, then radiation therapy would not be an option for the current patient, regardless of the ranking from the model. The DSS 18 also enables the care provider to assess the suitability of the references used for estimating the optimal treatment options for a patient. For example, if the patient is located in a particular geographical region that differs significantly from the geographical region where the source data are collected, then it would be inappropriate to recommend a treatment option to the patient based on that data.

The DSS 18 further provide information relating to additional testing and predicting how such additional treating can support the decision by modelling the narrowing of confidence intervals of outcome measures based on data on accuracy and precision of the test from available evidence, to make its predictive power actionable in the decision making process. For example, if doing diagnostic test X beyond the standard diagnostic tests provides new evidence that treatment Q will be more effective on the patient than treatments R or S, it is worthwhile to proceed with diagnostic test X.

In another embodiment, the DSS 18 utilizes provider-specific treatment delivery statistics instead of general statistics from the literature to reduce the confidence interval overlaps of treatment options to provide patients a provider-specific treatment decision support. This enables a care provider to adjust the confidence interval limits to account for intangible or difficult to capture information about the patient. The care provider also has the authority to assess the usefulness of the source data used to develop the model that estimates the optimal treatment option for the current patient to further personalize the system's output.

To accomplish such functionality, medical information system 16 stored information relating to an institution providing health advice (potentially among diagnostic and therapeutic services through healthcare professionals), applicable and available evidence in the form of a statistical or optimization model of the path of the patient's disease given certain health choices, and a computational decision aid application that is provided with data on the patient's preferences, preconditions and findings. The medical information system 16 further stores available evidence on alternative diagnostic or therapeutic methods that were not included in said the previous discussed statistical or optimization model, where this added evidence allows to the DSS 18 to compare the alternative methods to the ones employed in the previous discussed statistical model with regard to their accuracy and precision to inform the calculations within the model.

This comparison provided by the DSS 18 allows an estimate with potentially reduced variance of the outcome estimates that the statistical or optimization model predicts for each treatment choice based on the "standard" tests employed by the model if a particular or some "advanced" tests not included in the model but quantitatively comparable with the standard tests on accuracy, precision and predictive value would be applied. This functionality is made available to the user of the decision aid by the user interface element that allows to "evaluate the distinctive effect of additional tests", where the user can select a test or set of tests and see how the confidence intervals of the outcome predictions change (if they get narrower, the user might want to apply the test, otherwise the test is proven to be unnecessary).

Like an effective additional diagnostic test, provider-specific treatment delivery statistics can also improve the accuracy of outcome estimation. The provider-specific statistics may be obtained from insurance providers or the hospital/facility where the provider regularly performs the procedures of interest and the like. These statistics may include the severity of illness of the patient population that the provider generally treats, the rate of unpreventable complications due to patients' co-morbidities, among other factors. For example, some providers specialize in treating patients with specific co-morbidities, so if the patient has that co-morbidity, it could be beneficial to be treated by that provider.

In another embodiment, the user (e.g. patient or healthcare professional) gets to specify the acceptable confidence intervals or to set an acceptable level of 'overlap' for the outcomes of the individual treatment choices, and the DSS 18 chooses which additional tests would allow that. Basically this is the reverse of the approach described above: instead of 'if you do advanced diagnostic test A, then J is the outcome and you narrow the confidence interval by Y %', it would allow users to set 'I want to reduce overlap, what advanced diagnostic tests do I need to do?', or 'the maximum range of the confidence interval that I am willing to live with is +/−X %, what are options should I consider?', 'or the maximum acceptable overlap is Z %, what additional diagnostic tests should be done to get closest to achieve this?'. This would assume there are several new advanced diagnostic tests. While eliminating overlap in estimates of recommended treatment options may be difficult or impossible to achieve, reducing the overlap may be a satisfactory alternative. A response from the DSS 18 may be that no additional tests can reduce the overlap in estimates of recommended treatment options, and this would be a valid response from the system.

In yet another embodiment, other factors like additional costs per advanced diagnostic test might be taken into account. In another embodiment, the care provider can adjust the acceptable confidence intervals for patient prior to sharing the patient decision aid with the patient to account for intangible or difficult to capture personal information about the patient. In another embodiment, the care provider can assess the relevance of the source data used in the model that ranks the optimal treatment options for the current patient to ensure that only the most accurate and relevant information is used.

Figure 3:
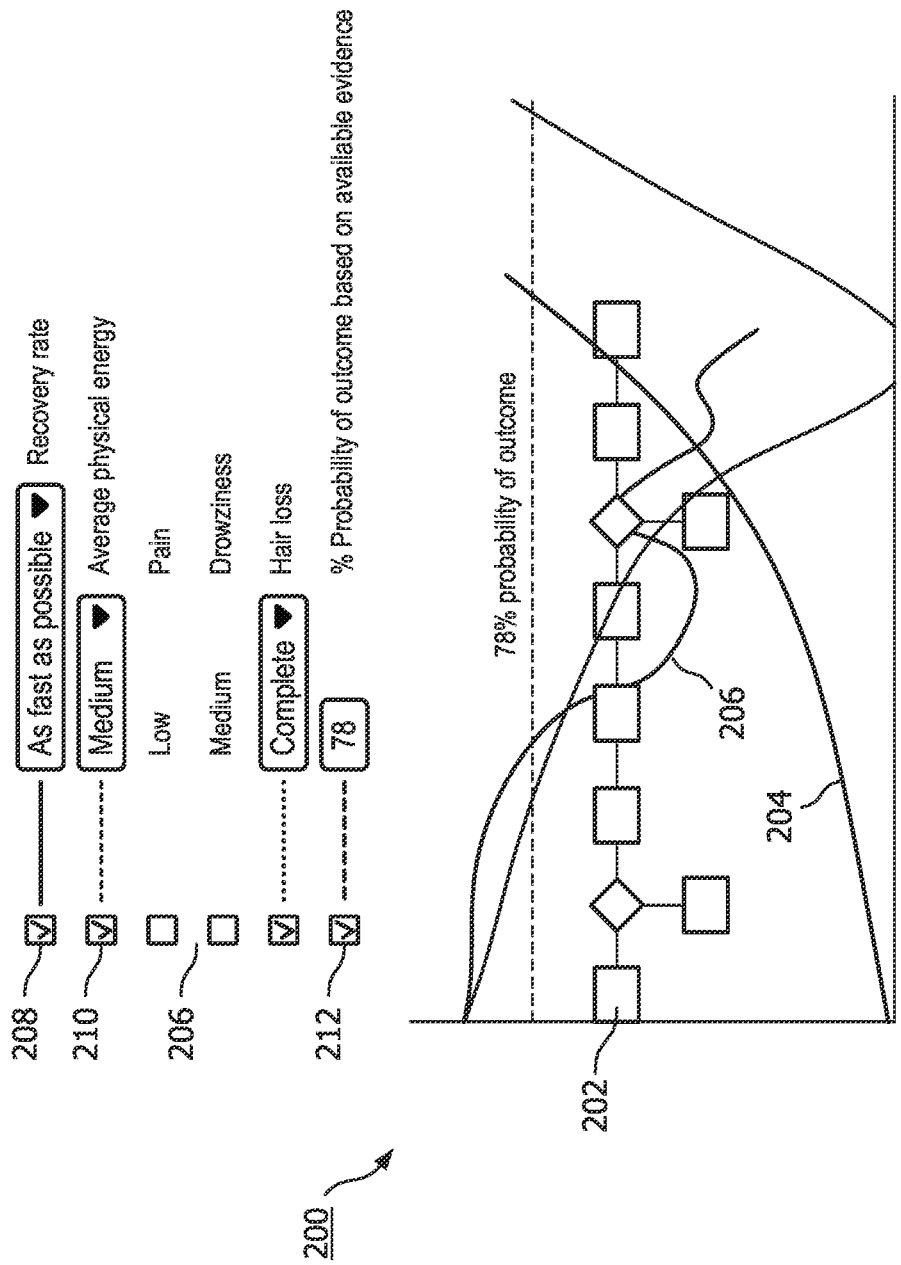
FIG. 3 is an interface for displaying a patient pathway in accordance with the present application.
Figure 4:
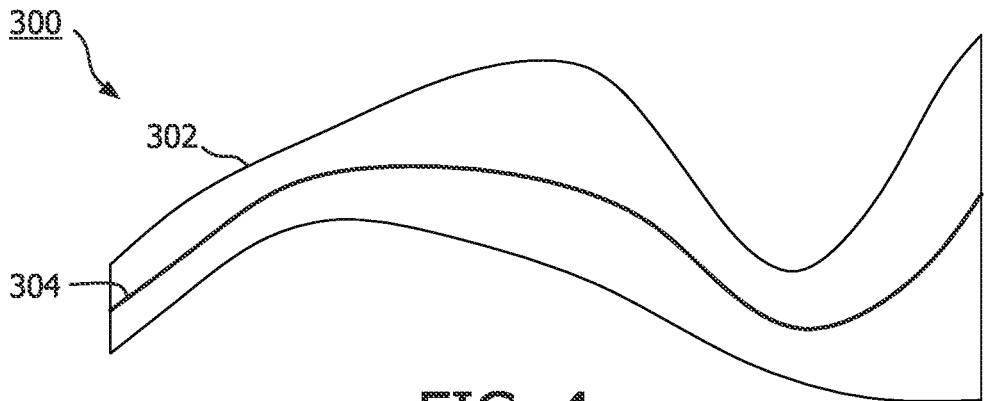
FIG. 4 is an interface displaying the confidence of the likelihoods of outcome in accordance with the present application.

FIG. 3 illustrates an interface 200 for displaying a patient pathway (e.g. a default one based on electronic health records (HER), preferences, medical guidelines of cancer type, etc.). The interface includes an overview 202 of the patient pathway along with the trends 204 of the outcomes parameters over time (e.g. recovery, side effects, etc.). The interface 200 also allows the patient to select various factors to display on the interface including side effects 206, recovery rate 208, energy level 210, and probability of outcome 212 of that particular outcome combination based on available evidence. It should be appreciated that the patient is able to adjust directly on the trends (e.g. dragging) and/or the patient pathway, and view the effect of the change on each other and on other outcome parameters, and on the probabilities. Adjustments can also be done via some other input mechanism (e.g. text entry, drop down box, etc.) for each parameter. FIG. 4 illustrates an interface 300 displaying the confidence 302 of the likelihoods of outcome over time 304.

Figure 5:
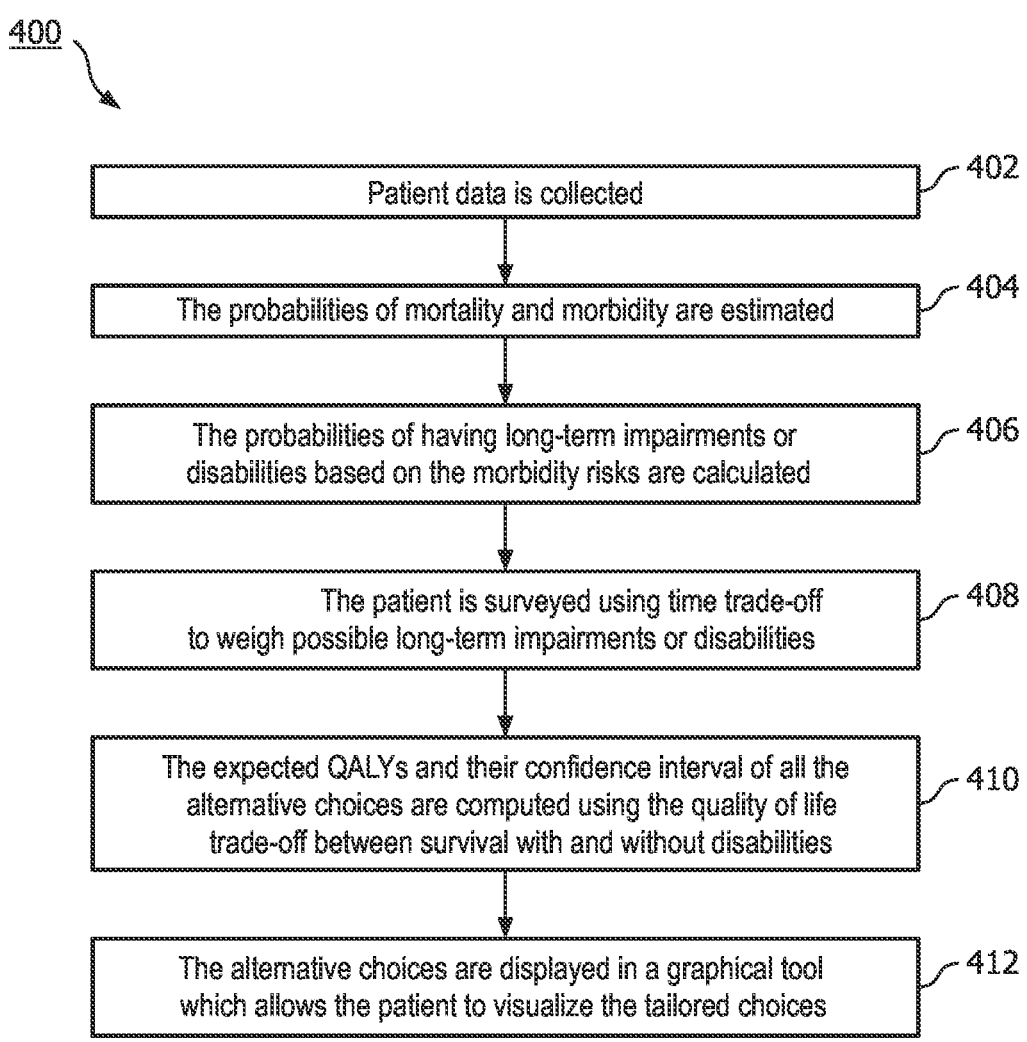
FIG. 5 is a flowchart diagram of a method for providing decision support for a patient in accordance with the present application.

With reference to FIG. 5, a flowchart diagram 400 of a method for providing decision support for a patient with localized prostate cancer is illustrated. Although each of the blocks in the diagram is described sequentially in a logical order, it is not to be assumed that the system processes the described information in any particular order or arrangement. At 402, patient data including the patient's race, age, family history of diseases, etc. are collected. At 404, the patient is surveyed using time-trade-off to weigh possible long-term impairments or disabilities. In case this step is skipped, the quality of life of having impairments or disabilities is computed using the national population-based estimates (for example, the estimate from Agency for Health Research and Quality (AHRQ)). At 406, the probabilities of having long term impairments or disabilities based on the morbidity risks are calculated. Specifically for prostate cancer patients, definitive treatments such as radical prostatectomy and radiation therapies are more likely to result in long term impairments or disabilities such as incontinence, erectile dysfunction, etc. Probabilities of having each of these long term impairments or disabilities are computed via the probabilities of having morbidities. At 408, the probabilities of mortality and morbidity (such as risk of infectious and non-infectious complications) are estimated based on patient counts in hospital's database (such as their prostatectomy registries) or medical literature for the population to which the patient belongs. At 410, the expected QALYs and their confidence interval of all the alternative choices are computed using the quality of life trade-off between survival with and without disabilities. Confidence intervals and the probabilities of an action being the best among all the alternatives are computed via stochastic sensitivity analysis, or other comparable method. At 412, the alternative choices are displayed in a graphical tool which allows the patient to visualize the tailored choices.

It should be appreciated that the present application be used to develop a personalized decision support system for different diseases. It could be used for both patient and surrogate decision making process, where the surrogate is a parent, spouse, or other health delegate. The present application also quantifies the alternative choices, and simplifies and shortens the shared decision making process, therefore reducing patients' stress, increasing the patients' satisfaction on their decisions, and ultimately reducing overall healthcare costs.

As used herein, a memory includes one or more of a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; or so forth. Further, as used herein, a processor includes one or more of a microprocessor, a microcontroller, a graphic processing unit (GPU), an application-specific integrated circuit (ASIC), a field-programmable gate array (FPGA), and the like; a user input device includes one or more of a mouse, a keyboard, a touch screen display, one or more buttons, one or more switches, one or more toggles, and the like; and a display device includes one or more of a LCD display, an LED display, a plasma display, a projection display, a touch screen display, and the like.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

Having thus described the preferred embodiments, the invention is now claimed to be:

1. A system for personalizing patient pathways, the system comprising:
   a display;
   one or more user input devices; and
   one or more processors programmed to:
   receive patient data relating to a patient's medical records;
   receive the patient's lifestyle values and preferences from the patient via the one or more user input devices;
   generate alternative options of patient pathway and treatment options using the patient data and the patient's lifestyle values and preferences including estimating probabilities of mortality and morbidity from the patient data, calculating probabilities of having long term impairments or disabilities based on the probabilities of morbidity, surveying the patient using time-trade-off to weigh the possible long-term impairments or disabilities, and calculating an expected quality-adjusted life years (QALYs) and confidence interval of the alternative choices using the time trade-off weighing the possible long-term impairments or disabilities; and
   generate a graphical tool that compares the alternative choices of pathway and treatment options including displaying, on the display, the alternative choices, QALYs, confidence intervals, and trends on health outcome including time of recovery, medical consequences, frequency and regime of treatment, lifestyle changes, and adverse effects;
   adjusting any one of the patient pathways and displaying the effect of that adjustment on the alternative choices, QALYs, confidence intervals, and trends of heath outcome;
   computing confidence intervals of the alternative outcomes based on the clinical evidences on outcomes, prognosis from similar populations, and personalized preferences on trading off quality of life and length of survival; and
   providing, on the graphical tool, best choices of pathways and treatment for the patient, wherein the best choices are based on the computed confidence intervals including providing a quantification of whether potential new information derived from an additional or new diagnostic test will help to determine the optimal treatment plan.

2. The system according to claim 1, wherein the graphical tool visualizes the choices of pathways and trends on health outcome for each pathway.

3. The system according to claim 1, wherein the probabilities of mortality and morbidity, probabilities of having long term impairments or disabilities, expected QALYs and their confidence interval are based on clinical evidences on outcomes and prognosis from similar populations.

* * * * *